United States Patent [19]
Iwamoto

[11] Patent Number: 5,134,376
[45] Date of Patent: Jul. 28, 1992

[54] A SOLUTION SPECIFIC CONDUCTIVITY METER AND METHOD FOR USE

[75] Inventor: Yasukazu Iwamoto, Kyoto, Japan

[73] Assignee: Horiba, Ltd., Kyoto, Japan

[21] Appl. No.: 603,794

[22] Filed: Oct. 26, 1990

[30] Foreign Application Priority Data

Oct. 28, 1989 [JP] Japan .................................. 1-126303

[51] Int. Cl.$^5$ ............................................ G01N 27/07
[52] U.S. Cl. .................................. 324/447; 324/449; 324/450
[58] Field of Search .............................. 324/446–450

[56] References Cited

U.S. PATENT DOCUMENTS

| | | | |
|---|---|---|---|
| 993,586 | 5/1911 | Digby et al. | 324/447 |
| 3,025,458 | 3/1962 | Eckfeldt et al. | 324/449 |
| 4,365,200 | 12/1982 | Goldsmith | 324/449 |

Primary Examiner—Jack B. Harvey
Attorney, Agent, or Firm—Price, Gess & Ubell

[57] ABSTRACT

A conductivity meter usable in solutions where the path of the electric lines of force between two electrodes is altered. In one embodiment, detachable guard rings alter the path length based upon their own conductivity. In another embodiment, the physical distance between the electrodes is altered while maintaining a constant electrode configuration.

12 Claims, 6 Drawing Sheets

PRIOR ART

A SOLUTION SPECIFIC CONDUCTIVITY METER AND METHOD FOR USE

FIELD OF THE INVENTION

The present invention relates to an apparatus and method for the measurement of conductivity or resistivity of solutions using the alternating current bi-pole method.

BACKGROUND OF THE INVENTION

In the measurement of a solution's conductivity or resistivity by the alternating current bi-pole method, an apparatus generally includes an electrode-supporting body and a pair of electrodes. The electrodes are disposed at certain predefined intervals from each other and from the electrode-supporting body. These distances are defined according to the particular solution's composition and concentration.

At the interface between the electrodes and the sample solution, an electric double layer is produced due to the separation of charges or the distance between the electrodes. Where the sample solution has a different composition or concentration than that for which the electrode distances are defined, a condenser capacitance (polarized capacitance) from the electric double layer produces a large error in the measurement.

To compensate for this error, the following actions have been taken: (a) the voltage applied between the electrodes has been changed; (b) different instruments where the surface area of the electrodes has been altered are used to customize the current density applied; or (c) the measuring frequency has been altered. These actions have not produced a more accurate probe, and merely change the resistivity between the poles or alter the cell constant.

In the prior art measurements of electrolyte solutions, different configurations were provided for similar solutions having different concentrations. Two or these configurations are illustrated in FIGS. 7 and 8.

FIG. 7 illustrates an apparatus for measuring the conductivity of high concentration solutions. An electrode-supporting body 50 has an elongated end which supports two electrodes 52. At the edges of the elongated end 53, covers 51 are provided. This H-shaped configuration provides a certain interval, or path length, L1 for current to travel through the high concentration solution.

FIG. 8 illustrates an apparatus for the measurement of conductivity of low concentration electrolyte solutions. An electrode-supporting structure 60 supports a base 63 which provides two electrodes 62. A sheath or cover 61 flares out from the end of the electrode-supporting structure 60. The path length L2 between the electrodes 62 in FIG. 8 is much less than the path length L1 between the electrodes 52 in FIG. 7. This operates to reduce the cell constant as much as possible in order to minimize both external induction and errors caused by electrostatic capacitance.

Thus, it has been necessary to provide separate devices for measuring the conductivity of solutions having different concentrations or different compositions. Furthermore, it has been necessary to use different conductivity devices having different cell constants, depending upon the concentration and composition of the solution. Where the conductivity of solutions is measured over a wide range of compositions and concentrations, it has been necessary to provide several types of measuring devices, different in form and construction, depending upon the conductivity of the solution.

OBJECTS OF THE INVENTION

It is therefore an object of the present invention to provide a method and apparatus for the measurement of the conductivity of solutions over a wide range of compositions and concentrations.

It is a further object of the present invention to provide a single conductivity measurement device for use in different solutions having different conductivities.

It is yet a further object of the invention to provide a method and apparatus for the measurement of conductivity of solutions where the configuration of electrodes never has to be changed.

SUMMARY OF THE INVENTION

These and other objects of the invention are generally provided by a conductivity measurement device wherein the electrode configuration is maintained, and the path that the current must travel through the solution between the electrodes is altered.

A conductivity meter according to the present invention may be illustrated by the preferred embodiment where an electrode-supporting body supports a pair of electrodes disposed at a suitably defined interval. In this embodiment, the electrode distance is permanent and several guard rings which cover the electrodes are provided for different solution compositions. For example, one guard ring may be formed of a conducting material, and a second guard ring may be formed of an insulating material. The guard rings may be detachably mounted on the electrode-supporting body.

Where the conductivity of a higher concentration solution is to be measured, the guard ring formed of insulating material is mounted on the electrode-supporting body. This insulated guard ring provides an increased path length of conduction through the solution, allowing an accurate conductivity measurement.

Where the conductivity of a low-concentration solution is to be measured, a guard ring formed of a conductor is mounted on the electrode-supporting body. The current travels from the electrodes through the solution to the conducting guard ring, which itself becomes part of the current path between electrodes. In this way, the path length of the current through the solution is reduced for a low-concentration electrolyte solution, and a more accurate conductivity measurement is provided.

Thus, the present invention provides a method and apparatus for the measurement of conductivity in different solutions using a single electrode configuration where the current path between the electrodes is altered for the solution of interest. The preferred embodiment alters the length of the current path through the solution. However, other changes in the current path between the electrodes may be used and will still come within the scope of the invention.

BRIEF DESCRIPTION OF THE DRAWINGS

The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein.

Figure 1:
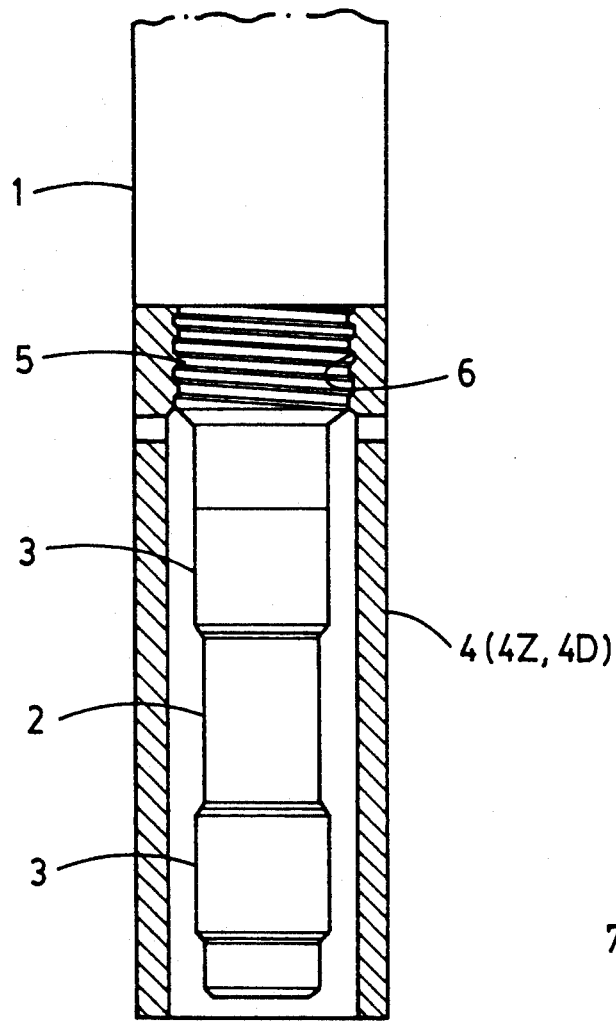
FIG. 1 is a longitudinal sectional view showing the main parts of a conductivity meter according to the preferred embodiment of the invention.
Figure 2:
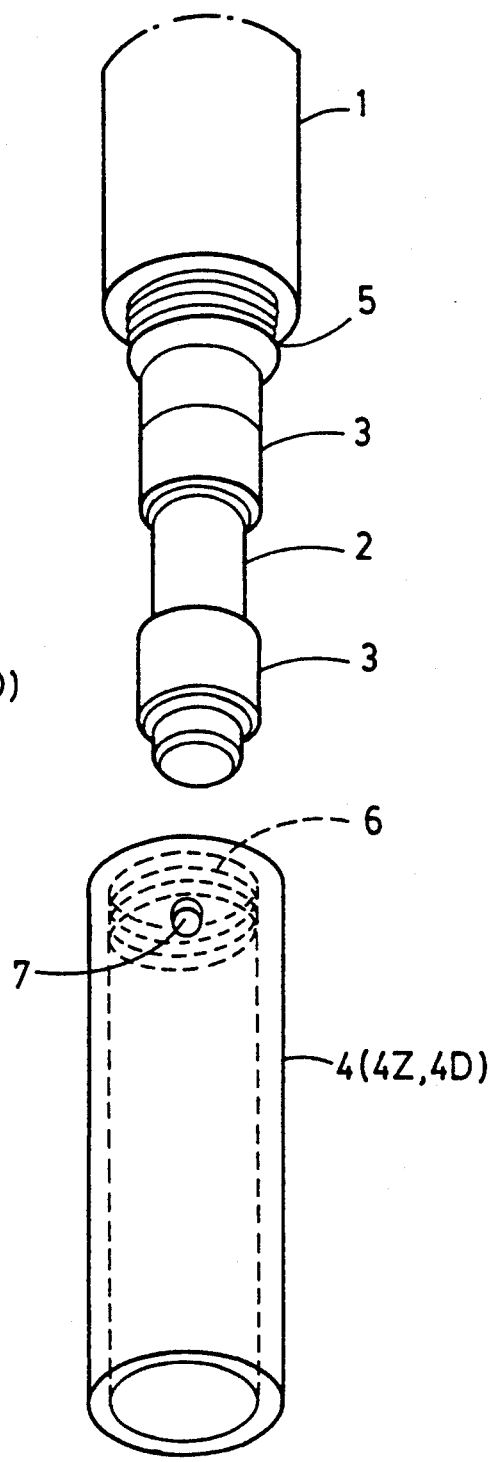
FIG. 2 is a perspective view showing the conductivity meter shown in FIG. 1.
Figure 3:
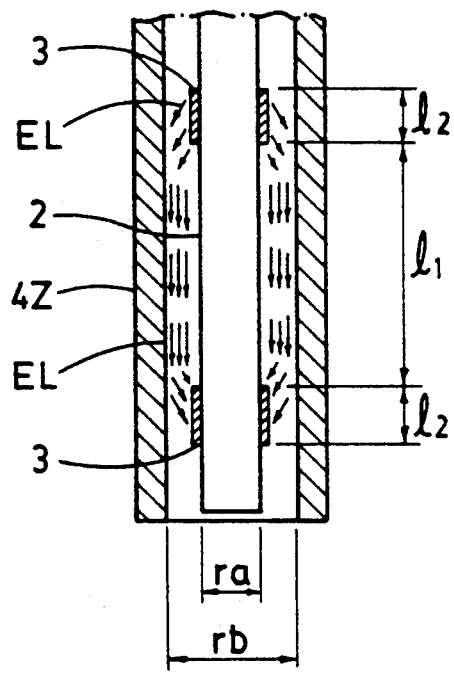
FIG. 3 is a cross-sectional diagram illustrating the operation of the preferred embodiment of the invention using an insulating guard ring.

Referring to FIGS. 1 and 2, showing main parts of a conductivity meter according to the preferred embodiment of the present invention, reference numeral 1 designates an electrode-supporting body formed of an insulating material, such as glass or plastic. A pair of tubular electrodes 3, 3 are attached to a rod-like portion 2. The electrodes 3, 3 have an outside diameter of $r_a$ and a width of $L_2$ as shown in FIG. 3. The electrodes 3, 3 are spaced at an interval $L_1$.

When measuring an electrolyte solution, it is preferable that the electrodes 3, 3 are made of platinum when the electrode-supporting body 1 is made of glass, and that the electrodes are made of stainless steel when the electrode-supporting body 1 is made of plastic.

Reference numeral 4 designates tubular guard rings (having an inside diameter of $r_b$ shown in FIG. 3) covering the electrodes 3, 3. The guard rings regulate electric lines of force (shown by EL in FIGS. 3 and 4) produced between the electrodes 3, 3 when an alternating current voltage is applied between the electrodes 3, 3 for measurement.

The upper side of the guard ring 4 has a female screw portion 6 which is screwed onto a male screw portion 5 formed in the rod-like portion 2. A vent hole 7 is provided in the guard ring 4. The vent hole 7 opens below the female screw portion 6, allowing air to escape when the apparatus of the preferred embodiment is placed into the solution.

In the preferred embodiment, the guard rings 4 have one form and size, and each is made of a different material. One guard ring 4 is made of an insulating material, such as plastic or glass, and a second guard ring is made of a conductor such as stainless steel. Hereinafter the guard ring 4, which is made of an insulating material, will be designated by reference numeral 4Z, and the guard ring 4, made of a conductor, will be designated by the reference numeral 4D.

Where the conductivity of a high-concentration electrolyte solution is measured, the guard ring 4Z, made of an insulating material, is mounted on the electrode-supporting body 1 and immersed in the solution.

Figure 4:
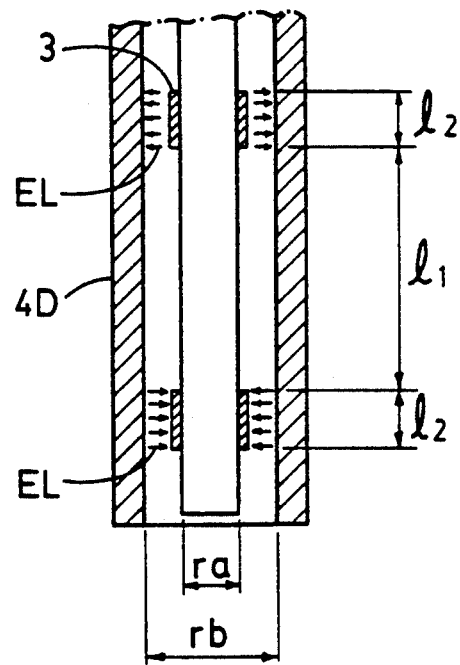
FIG. 4 is a cross-sectional diagram illustrating the operation of the preferred embodiment of the invention using a conducting guard ring.

The operation of the probe is shown in FIG. 3. Upon the application of an alternating current voltage between the electrodes 3, 3, the electric lines of force EL pass through a gap between the electrode-supporting body 1 and the guard ring 4Z. An apparatus or cell constant $C_1$ is expressed by the following equation:

$$C_1 = L_1/\pi(r_b^2 - r_a^2) \text{ [cm}^{-1}\text{]}$$

Where the conductivity of a low-concentration solution is measured, the guard ring 4D, made of a conductor, is mounted on the electrode-supporting body 1 and immersed in the solution. The operation of the probe is shown in FIG. 4. Upon the application of an alternating current voltage between the electrodes 3, 3, electric lines of force EL are produced. As shown in the figure, the electric lines of force EL flow out of the electrodes 3, 3 and into the guard ring 4D. Thus, the distance that the electric lines of force EL travel through the solution is shortened from the distance shown in FIG. 3. An apparatus or cell constant $C_2$ for the conducting guard ring is expressed by the following equation:

$$C_2 = 1/(\pi L_2 \cdot \log r_b/r_a) \text{ [cm}^{-1}\text{]}$$

Thus, for identical electrode configurations, different apparatus or cell constants may be produced. Upon substituting $r_a = 0.5$ cm, $r_b = 0.65$ cm, $L_1 = 5.4$ cm and $L_2 = 0.36$ cm in the respective equations, the different guard rings will produce cell constants $C_1 = 10$ [cm$^{-1}$] and $C_2 = 0.1$ [cm$^{-1}$]. Thus, guard rings having the same form and size can be used on one probe to allow it to be used for different solutions. One guard ring 4Z can be used for the measurement of the high-concentration solution, while the other guard ring 4D can be used for the measurement of the low-concentration solution. One electrode-supporting body 1 is maintained, and the guard rings 4Z, 4D mounted on the electrode-supporting body 1 are merely exchanged when different solutions are measured.

Although the conducting guard ring 4D is made of stainless steel in the preferred embodiment, a body of the guard rings may be formed from an insulating material, and a suitable metal, such as nickel, may be plated on a surface of the guard rings. The conductivity meter can then also be used for the measurement of solutions having relatively low concentration.

Figure 9:
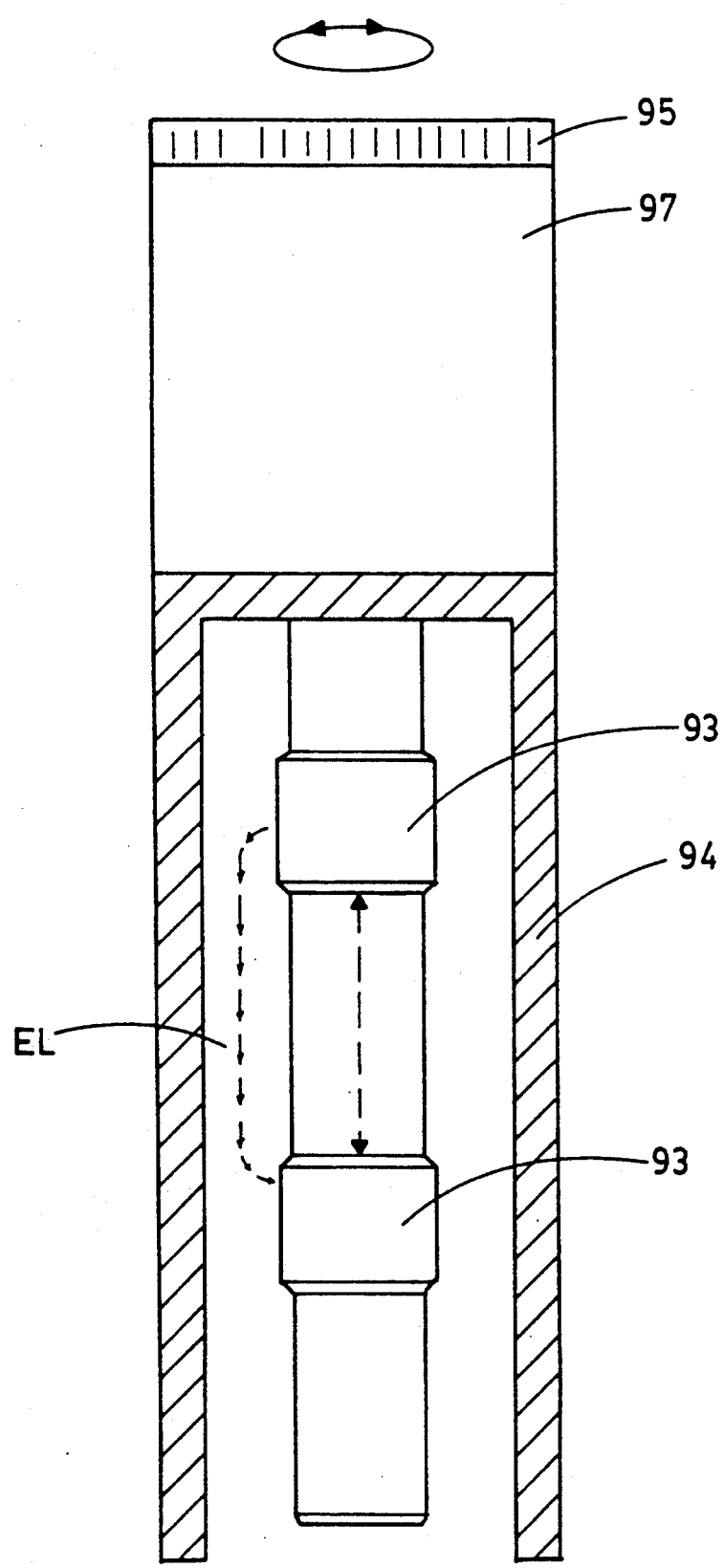
FIG. 9 is an illustration of a second embodiment of the invention.

A further embodiment of the invention is shown in FIG. 9, wherein the electrode configuration is maintained and a single guard ring 94 may be permanently installed for many solutions. In this embodiment, the guard ring 94 is an insulator forcing the electric lines of force EL to travel between the electrodes 93 through the solution.

The path length of the electric lines of force EL is altered by changing the distance between the electrodes 93. This is accomplished using a screw mechanism 95 attached to the handle 97. The screw may have an indicator to allow easy calibration for solutions having different concentrations and compositions.

Figure 5:
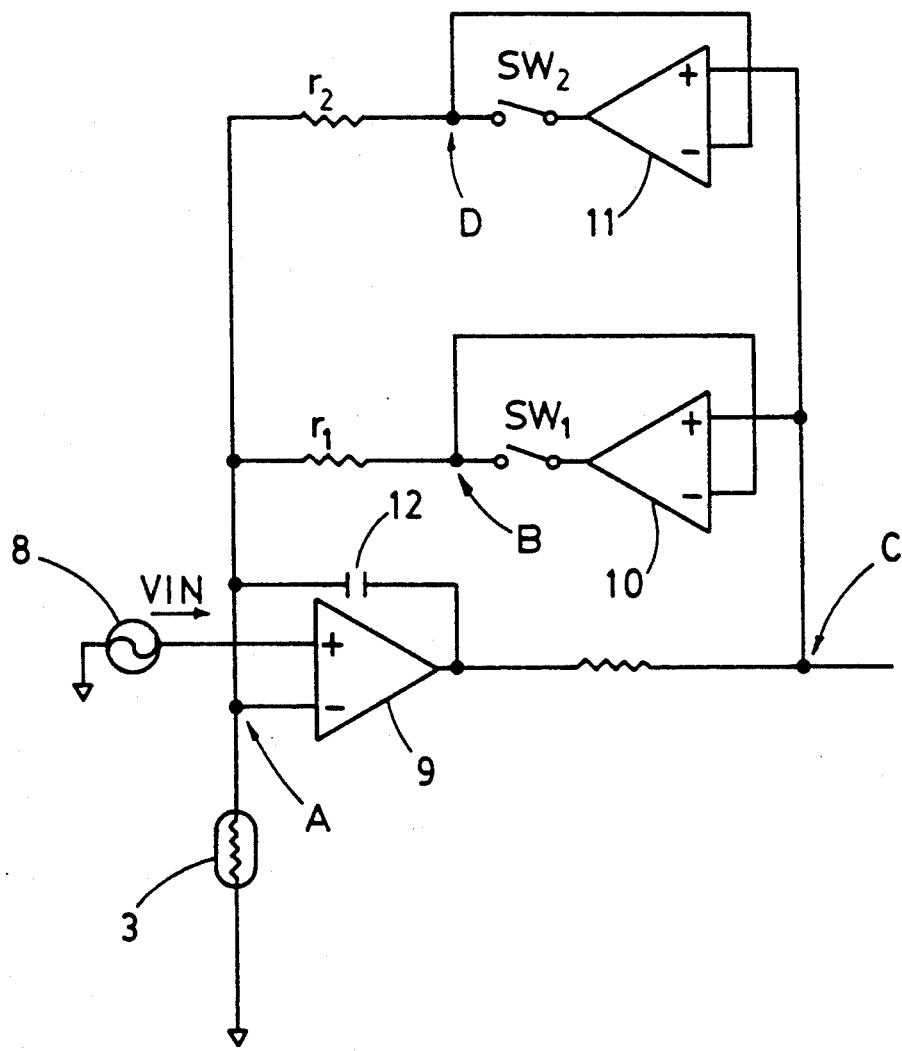
FIG. 5 is a circuit diagram illustrating a conductivity-measuring and detecting circuit used in the preferred embodiment of the invention.

FIG. 5 shows a conductivity-measuring and detecting circuit used in the conductivity meter of the preferred embodiment. Reference numeral 8 designates an oscillator applying a voltage input. Reference numeral 9 designates an operational amplifier. $r_1$, $r_2$ designate gain resistances. SW1, SW2 designate analog switches. Reference numerals 10, 11 designate further operational amplifiers.

Where a conductivity range is to be selected by the gain resistance $r_1$, the analog switch SW1 is turned on and the analog switch SW2 is turned off, so that the gain resistance $r_2$ has no effect.

A voltage $V_{IN}$ from the oscillator 8 to the plus terminal of the operational amplifier 9 is used as a signal input. A voltage at a point A where the electrode 3 is connected will then also be $V_{IN}$. Reference numeral 12 designates an oscillation-preventing condenser connected along the feedback portion of the operational amplifier 9. Therefore, if the resistance of the electrode 3 is $R_T$, a voltage $V_S$ at a point B is expressed by the following equation:

$$V_S = V_{IN} \times (1 + r_1/R_T)$$

Since switch SW1 is closed and switch SW2 is open, the voltage $V_D$ at a point D is expressed by the following equation:

$$V_D = V_{IN}$$

Therefore, the voltage $V_c$ at the output point C is expressed by the following equation:

$$V_c = V_{IN} \times (1 + r_1/R_T);$$

and the gain to the output $V_c$ is changed merely by altering the gain resistance $r_1$.

Figure 6:
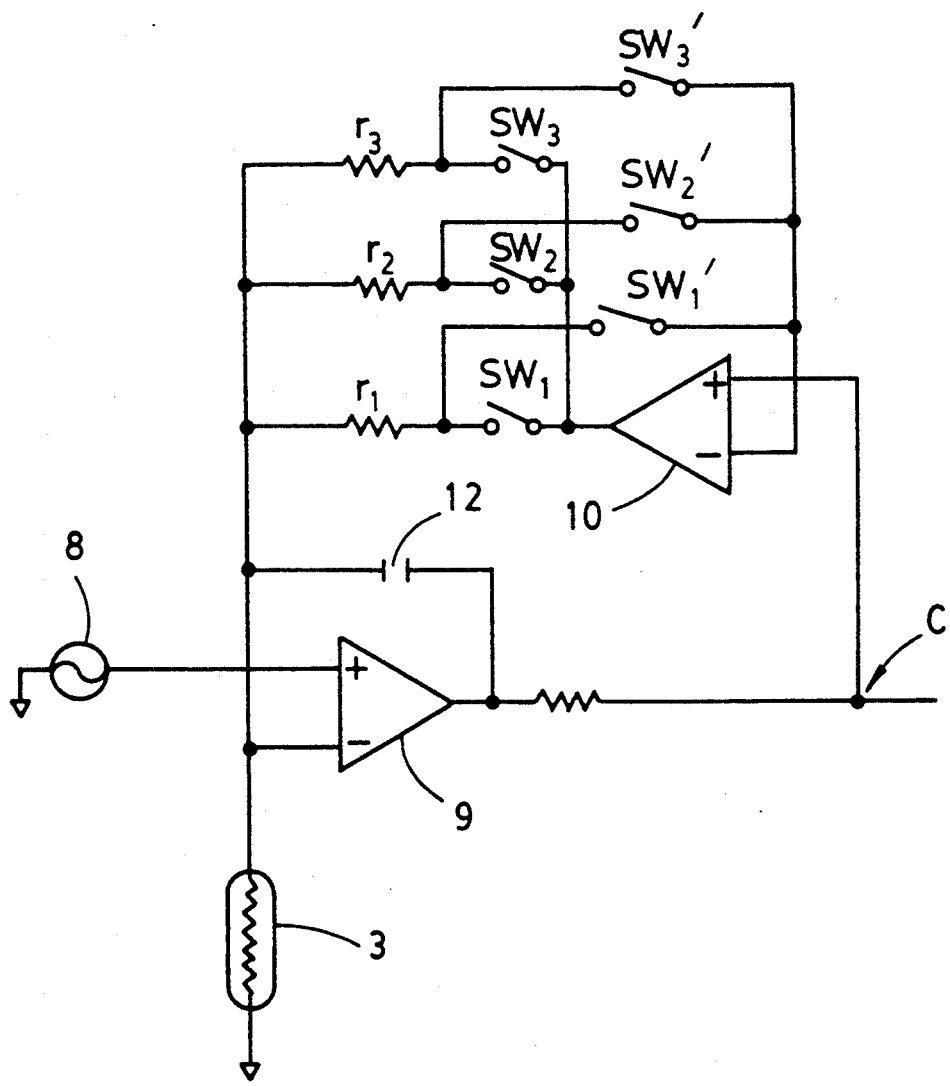
FIG. 6 is a circuit diagram illustrating a conductivity-measuring and detecting circuit used in the preferred embodiment of the invention.
Figure 7:
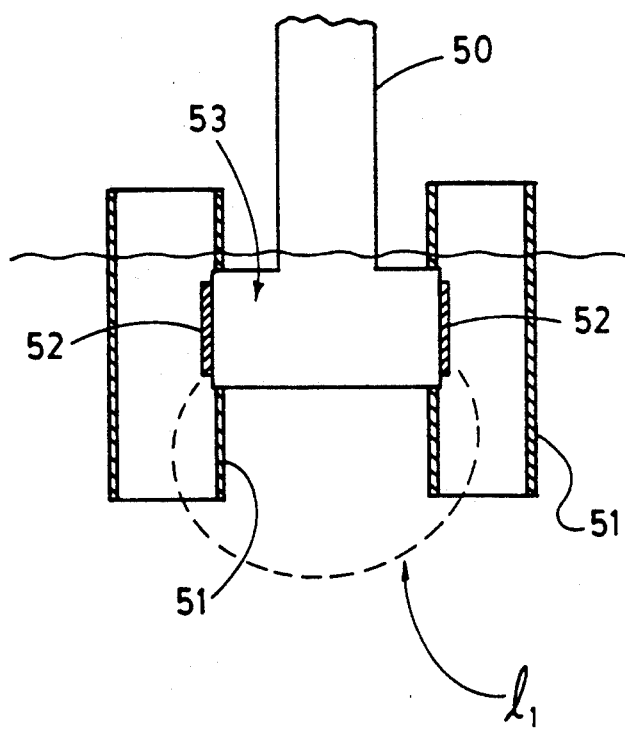
FIG. 7 is a diagram showing a prior art conductivity-measuring device.
Figure 8:
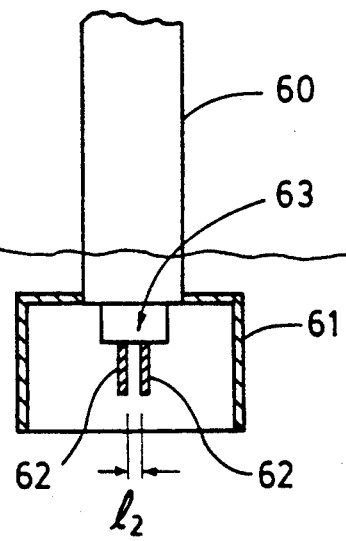
FIG. 8 is a diagram showing a prior art conductivity-measuring device.

FIG. 6 shows another example of a conductivity-measuring and detecting circuit for use in the preferred embodiment of the invention. The basic circuit is common to FIG. 6 and FIG. 5. Equivalent reference numerals show members which are the same between the figures.

In the circuit shown in FIG. 6, only one operational amplifier 10 is used. Analog switches SW1, SW2, and SW3 and gain resistances $r_1$, $r_2$, and $r_3$ are respectively connected with the output portion of this operational amplifier 10 in series. The respective series connections are connected with each other in parallel and, further, the analog switches SW1, SW2, and SW3 are connected with the gain resistances $r_1$, $r_2$, and $r_3$ through analog switches SW1', SW2', and SW3', respectively. Thus, only one operational amplifier 10 is connected with the feedback portion of the operational amplifier 9.

Changing the circuit gain in the detecting circuit shown in FIG. 6 uses the same procedure as that in the detecting circuit shown in FIG. 5.

These circuits which alter the gain in the measuring and detecting circuit in the preferred embodiment are merely illustrative of possible circuits. Further circuits may be readily apparent from these to one skilled in the art.

As shown in the preferred embodiment, the conductivity of the solution can be measured over a wide range by merely exchanging the guard ring made of an insulating material and the guard ring made of a conductor, which both have equivalent shapes and dimensions and may be secured to a single electrode-supporting body. It is unnecessary to select from several probes a particular conductivity probe to be used depending upon the conductivity of the solution. Thus, the present invention eliminates the need for several conductivity probes of different configurations and provides a single method and apparatus adaptable to many situations. The configuration of the electrodes in the probe of the preferred embodiments stays the same in all measurements, and it is merely necessary to change detachable guard rings or keep a single guard ring and alter the distance between the electrodes in a single configuration within the probe.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A conductivity meter, comprising an electrode-supporting body having a pair of electrodes disposed at a suitable interval, a plurality of interchangeable guard rings, each guard ring formed of materials having a different conductivity, which guard rings are each detachably mountable on said electrode-supporting body to cover said electrodes, only one guard ring being mounted at any one time, the mounted guard ring being selected based upon a range of conductivity of a solution to be measured.

2. A meter for measuring the conductivity of different solutions in which the meter may be immersed, comprising:
   (a) an electrode supporting body;
   (b) at least two electrodes attached to the electrode supporting body, the two electrodes separately disposed and having a predefined configuration;
   (c) energizing means for energizing the electrodes;
   (d) circuit means for detecting conductivity of a solution through which electric lines of force must travel between the electrodes; and
   (e) altering means for altering a path through the solution which the electric lines of force must travel between the electrodes, the path being altered based upon a range of conductivity of the solution to be measured.

3. The apparatus of claim 2, wherein the path length is altered.

4. The apparatus of claim 3, wherein the altering means includes a plurality of interchangeable guard rings, each guard ring formed of material having a different conductivity, the guard rings being detachably mountable on the electrode supporting body, and only one guard ring being mounted at any one time, the mounted guard ring being selected based upon the range of conductivity of the solution to be measured.

5. The apparatus of claim 4, wherein one of the guard rings is an insulator.

6. The apparatus of claim 5, wherein one of the guard rings is a conductor.

7. The apparatus of claim 2, wherein the altering means is a means for altering the distance between the electrodes.

8. A method for testing the conductivity of different solutions using a conductivity meter having a predefined electrode configuration comprising the steps of immersing the meter in a solution, altering the path between electrodes that electric lines of force travel through the solution to be measured, the path being altered based upon a range of conductivity of the solution to be measured, energizing the electrodes, and determining the conductivity of the solution from the electric lines of force.

9. The method of claim 8, wherein the path length is altered.

10. The method of claim 9, wherein a plurality of interchangeable guard rings are provided to be mounted over the electrodes, each guard ring having a different conductivity, only one guard ring being mounted at any one time, and further including the step of interchanging the guard rings to mount a guard ring necessary for the solution.

11. The method of claim 10, further comprising the steps of mounting a guard ring having higher conductivity for lower concentration electrolyte solutions, and mounting a guard ring having lower conductivity for higher concentration electrolyte solutions.

12. The method of claim 9, wherein the path length is altered by changing the distance between the electrodes.

* * * * *